United States Patent
Johnson et al.

(10) Patent No.: US 12,064,233 B2
(45) Date of Patent: Aug. 20, 2024

(54) FALL DETECTION USING SENSORS IN A SMART MONITORING SAFETY SYSTEM

(71) Applicant: CareView Communications, Inc., Lewisville, TX (US)

(72) Inventors: Steven Gail Johnson, Highland Village, TX (US); Derek del Carpio, Corinth, TX (US); James M. Fathman, Carrollton, TX (US)

(73) Assignee: CareView Communications, Inc., Lewisville, TX (US)

( * ) Notice: Subject to any disclaimer, the term of this patent is extended or adjusted under 35 U.S.C. 154(b) by 0 days.

(21) Appl. No.: 17/037,845

(22) Filed: Sep. 30, 2020

(65) Prior Publication Data

US 2021/0022649 A1    Jan. 28, 2021

Related U.S. Application Data

(63) Continuation of application No. 16/389,237, filed on Apr. 19, 2019, now Pat. No. 10,827,951.

(Continued)

(51) Int. Cl.
| | |
|---|---|
| *G08B 21/02* | (2006.01) |
| *A61B 5/00* | (2006.01) |
| *A61B 5/11* | (2006.01) |
| *G08B 21/04* | (2006.01) |
| *G08B 25/10* | (2006.01) |

(52) U.S. Cl.
CPC .......... *A61B 5/1117* (2013.01); *A61B 5/0022* (2013.01); *A61B 5/0024* (2013.01); *G08B 21/02* (2013.01); *G08B 21/0446* (2013.01); *G08B 25/10* (2013.01); *G08B 21/043* (2013.01)

(58) Field of Classification Search
CPC ... A61B 5/1117; A61B 5/0022; A61B 5/0024; G08B 21/02; G08B 21/0446; G08B 21/043
See application file for complete search history.

(56) References Cited

U.S. PATENT DOCUMENTS

| | | | |
|---|---|---|---|
| 6,696,956 B1 * | 2/2004 | Uchida | G08B 21/0423 340/539.18 |
| 2012/0314901 A1 * | 12/2012 | Hanson | G16H 40/67 600/595 |

(Continued)

*Primary Examiner* — Benyam Haile
(74) *Attorney, Agent, or Firm* — Meister Seelig & Fein PLLC

(57) ABSTRACT

A smart monitoring system comprising a plurality of sensor devices coupled to appliances and fixtures within a dwelling environment, where at least one of the plurality of sensor devices comprises sensor elements including an accelerometer. The system further comprising a computing device operative to receive event signals from the plurality of sensor devices, identify a possible fall event from one or more of the plurality of sensor devices based on the event signals, sample sensor data from one or more of the plurality of sensor devices wherein the sensor data includes measurements of movement. The computer device is further operative to determine a fall has occurred based on the sampled sensor data, sample additional sensor data from the one or more of the plurality of sensor devices for additional motion at a period of time subsequent to the possible fall event, and determine a recovery from the fall based on the additional sensor data.

20 Claims, 8 Drawing Sheets

Related U.S. Application Data

(60) Provisional application No. 62/659,858, filed on Apr. 19, 2018.

(56) References Cited

U.S. PATENT DOCUMENTS

| | | | |
|---|---|---|---|
| 2015/0068069 A1* | 3/2015 | Tran | A43B 13/183 |
| | | | 36/136 |
| 2015/0302539 A1* | 10/2015 | Mazar | G08B 21/02 |
| | | | 705/3 |
| 2016/0187368 A1* | 6/2016 | Modi | G01P 21/00 |
| | | | 702/141 |
| 2017/0168095 A1* | 6/2017 | Shinkle | G01R 17/02 |

* cited by examiner

FALL DETECTION USING SENSORS IN A SMART MONITORING SAFETY SYSTEM

CROSS-REFERENCE TO RELATED APPLICATIONS

The present application is related to the following patents and applications, which are assigned to the assignee of the present invention:
a. U.S. Pat. No. 7,477,285, filed Dec. 12, 2003, entitled "Non-intrusive data transmission network for use in an enterprise facility and method for implementing,"
b. U.S. Pat. No. 8,471,899, filed Oct. 27, 2009, entitled "System and method for documenting patient procedures,"
c. U.S. Pat. No. 8,675,059, filed Jul. 29, 2010, entitled "System and method for using a video monitoring system to prevent and manage decubitus ulcers in patients,"
d. U.S. Pat. No. 8,676,603, filed Jun. 21, 2013, entitled "System and method for documenting patient procedures,"
e. U.S. Pat. No. 9,041,810, filed Jul. 1, 2014, entitled "System and method for predicting patient falls,"
f. U.S. application Ser. No. 12/151,452, filed May 6, 2008, entitled "System and method for predicting patient falls,"
g. U.S. application Ser. No. 14/039,931, filed Sep. 27, 2013, entitled "System and method for monitoring a fall state of a patient while minimizing false alarms,"
h. U.S. application Ser. No. 13/429,101, filed Mar. 23, 2012, entitled "Noise Correcting Patient Fall Risk State System and Method for Predicting Patient Falls,"
i. U.S. application Ser. No. 13/714,587, filed Dec. 14, 2012, entitled "Electronic Patient Sitter Management System and Method for Implementing,"
j. U.S. application Ser. No. 14/158,016, filed Jan. 17, 2014, entitled "Patient video monitoring systems and methods having detection algorithm recovery from changes in illumination,"
k. U.S. application Ser. No. 14/188,396, filed Feb. 24, 2014, entitled "System and method for using a video monitoring system to prevent and manage decubitus ulcers in patients,"
l. U.S. application Ser. No. 14/213,163, filed Mar. 13, 2014, entitled "System and method for documenting patient procedures,"
m. U.S. application Ser. No. 14/209,726, filed Mar. 14, 2014, entitled "Systems and methods for dynamically identifying a patient support surface and patient monitoring,"
n. U.S. application Ser. No. 14/710,009, filed May 12, 2015, entitled "Electronic Patient Sitter Management System and Method for Implementing,"
o. U.S. application Ser. No. 15/332,283, filed Oct. 24, 2016, filed Oct. 22, 2015, entitled "PATIENT VIDEO MONITORING SYSTEMS AND METHODS FOR THERMAL DETECTION OF LIQUIDS," and
p. U.S. application Ser. No. 15/364,872, filed Nov. 20, 2016, entitled "SYSTEM AND METHOD FOR PREDICTING PATIENT FALLS."

This application claims the priority of U.S. Provisional Application No. 62/659,858, filed on Apr. 19, 2018, entitled "SMART MONITORING SAFETY SYSTEM USING SENSORS."

The above identified patents and applications are incorporated by reference herein in their entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND OF THE INVENTION

Field of the Invention

This application generally relates to a smart monitoring system, and in particular, a plurality of devices, including intelligent-sensing network-connected devices, that communicate with each other and/or with a central server or a cloud-computing system to provide safety and improved quality of life.

Description of the Related Art

Healthcare monitoring suffers from the disadvantage of requiring staff if the monitoring is to be in the form of direct observation. A closed-circuit visual and/or audio feed monitor requires a caregiver to be vigilant about monitoring the feed to sense the problem in the distant room. Thus, the trend in patient monitoring has been toward the use of electrical devices to signal changes in a patient's circumstance to a caregiver who might be located either nearby or remotely at a central monitoring facility, such as a nurse's station. An automated hospital care system improves quality of care and reduces chance for errors.

Patients are increasingly being monitored, cared for, and/or treated outside a conventional hospital environment. For example, home healthcare is growing trend wherein patients are monitored and treated from their homes. Home healthcare is generally less expensive and also frees up hospital resources allowing the hospital to focus on patients with more critical needs. However, among other worries, family members and health care professionals are concerned about patient forgetfulness (e.g., not remembering to take medication), confusion (e.g., taking an incorrect dosage of medication), wellness monitoring (e.g., making sure the patient has not become incapacitated), and ability to summon help (e.g., sending an alarm in an emergency). Thus, there exists a need for a smart monitoring system that would address and solve the above-described problems to improve safety and quality of life.

SUMMARY OF THE INVENTION

The present application discloses smart monitoring method and systems. According to one embodiment, a smart monitoring system comprises a plurality of sensor devices coupled to appliances and fixtures within a dwelling environment, where at least one of the plurality of sensor devices comprising sensor elements including an accelerometer. The system further comprises a computing device operative to receive event signals from the plurality of sensor devices, identify a possible fall event from one or more of the plurality of sensor devices based on the event signals, sample sensor data from the one or more of the plurality of sensor devices, wherein the sensor data includes measurements of movement. The computing device is further operative to determine a fall has occurred based on the sampled sensor data, sample additional sensor data from the one or more of the plurality of sensor devices for additional motion at a period of time subsequent to the possible fall event, determine a presence of recovery from the fall based on the additional sensor data, generate notifications for an alarm based on the determination of the fall, and transmit the notifications over a communication network to a client device, wherein the alarm activates a web interface to cause the alarm to display on the client device and to enable a connection from the client device to the computing device.

In one embodiment, the computing device is further configured to determine an absence of the recovery from the fall based the additional sensor data and generate an alert based on the absence of the recovery. The alert may be transmitted to at least one of a central monitoring location, emergency contact, medical staff, care provider, and a call operator. The sensor data may include real-time measurements of movement. Alternatively, the sensor data may include measurements of movement at a time of occurrence of the possible fall event. The measurements of movement may comprise a delta sum of absolute displacement values of movement along a plurality of coordinate axis. In another embodiment, the computing device is further configured to compare the measurements of movement within a given time window with one or more patterns. The one or more patterns may correspond to movements associated with events selected from the group consisting of: a fall with recovery, a fall without recovery, or non-fall events.

In certain embodiments, the appliances and fixtures are selected from the group consisting of a toilet, a door, a window, a refrigerator, a television remote, and a medicine cabinet. The computing device may receive the event signals from a sensor device coupled to a handle of the toilet, and determine flushing of the toilet based on the event signals from the sensor device coupled to the handle of the toilet. Another embodiment may include the computing device receiving the event signals from a sensor device coupled to the door, and determining an opening or closing of the door based on the event signals from the sensor device coupled to the door. Yet another embodiment includes the computing device receiving the event signals from a sensor device coupled to the window, and determining an opening or closing of the window based on the event signals from the sensor device coupled to the window.

The computing device may also receive the event signals from a sensor device coupled to the refrigerator, and determine an opening or closing of the refrigerator based on the event signals from the sensor device coupled to the refrigerator. The computing device is also able to receive the event signals from a sensor device coupled to the television remote, and determine watching of a television based on the event signals from the sensor device coupled to the television remote. Additionally, the computing device can be configured to receive the event signals from a sensor device coupled to the medicine cabinet, and determine an individual taking medicine based on the event signals from the sensor device coupled to the medicine cabinet.

According to another embodiment, the system comprises a processor and a memory having executable instructions stored thereon that when executed by the processor cause the processor to receive event signals from a plurality of sensor devices, the plurality of sensor devices coupled to appliances and fixtures within a dwelling environment, and at least one of the plurality of sensor devices comprising sensor elements including an accelerometer. The processor may be further configured to identify a possible fall event from one or more of the plurality of sensor device based on the event signals, sample sensor data from the one or more of the plurality of sensor devices, the sensor data including measurements of movement, determine a fall has occurred based on the sampled sensor data, sample additional sensor data from the one or more of the plurality of sensor devices for additional motion at a period of time subsequent to the possible fall event, determine a presence of recovery from the fall based on the additional sensor data, generate notifications for an alarm based on the determination of the fall and the presence of recovery, and transmit the notifications over a communication network to a client device, wherein the alarm activates a web interface to cause the alarm to display on the client device and to enable a connection from the client device to the processor.

According to one embodiment, the method comprises receiving, by a computing device, event signals from a plurality of sensor devices, the plurality of sensor devices coupled to appliances and fixtures within a dwelling environment, at least one of the plurality of sensor devices comprising sensor elements including an accelerometer, identifying, by the computing device, a possible fall event from one or more of the plurality of sensor device based on the event signals, sampling, by the computing device, sensor data from the one or more of the plurality of sensor devices, the sensor data including measurements of movement, determining, by the computing device, a fall has occurred based on the sampled sensor data, sampling, by the computing device, additional sensor data from the one or more of the plurality of sensor devices for additional motion at a period of time subsequent to the possible fall event, determining, by the computing device, a presence of recovery from the fall based on the additional sensor data, generating, by the computing device, notifications for an alarm based on the determination of the fall and the presence of recovery, and transmitting, by the computing device, the notifications over a communication network to a client device, wherein the alarm activates a web interface to cause the alarm to display on the client device and to enable a connection from the client device to the computing device.

The method may further comprise determining an absence of the recovery from the fall based the additional sensor data and generating an alert based on the absence of the recovery. The alert may be transmitted to at least one of a central monitoring location, emergency contact, medical staff, care provider, and a call operator. The measurements of movement may comprise a delta sum of absolute displacement values of movement along a plurality of coordinate axis.

BRIEF DESCRIPTION OF THE DRAWINGS

The invention is illustrated in the figures of the accompanying drawings which are meant to be exemplary and not limiting, in which like references are intended to refer to like or corresponding parts, and in which.

DETAILED DESCRIPTION OF THE INVENTION

Subject matter will now be described more fully hereinafter with reference to the accompanying drawings, which form a part hereof, and which show, by way of illustration, exemplary embodiments in which the invention may be practiced. Subject matter may, however, be embodied in a variety of different forms and, therefore, covered or claimed subject matter is intended to be construed as not being limited to any example embodiments set forth herein; example embodiments are provided merely to be illustrative. It is to be understood that other embodiments may be utilized and structural changes may be made without departing from the scope of the present invention. Likewise, a reasonably broad scope for claimed or covered subject matter is intended. Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of exemplary embodiments in whole or in part. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

The present disclosure relates to facilitating management of healthcare, safety, and well-being, including monitoring and assessing the quality of patient care, and provides data, reports, analytics, etc. related thereto. The invention provides embodiments of systems and methods which facilitate management of health care at home or provided by a facility, e.g., assisted living or long-term care homes. Embodiments of the present disclosure generally relate to a plurality of devices, including intelligent-sensing network-connected devices, that communicate with each other and/or with a central server or a cloud-computing system for monitoring and assessing safety and quality of life of patients or cared-for individuals. In particular, a smart monitoring environment is disclosed that increases awareness around an individual and improves safety by leveraging multiple sensors that work in conjunction to help identify and describe information about the individual, specifically with regards to safety and quality of life.

Figure 1:
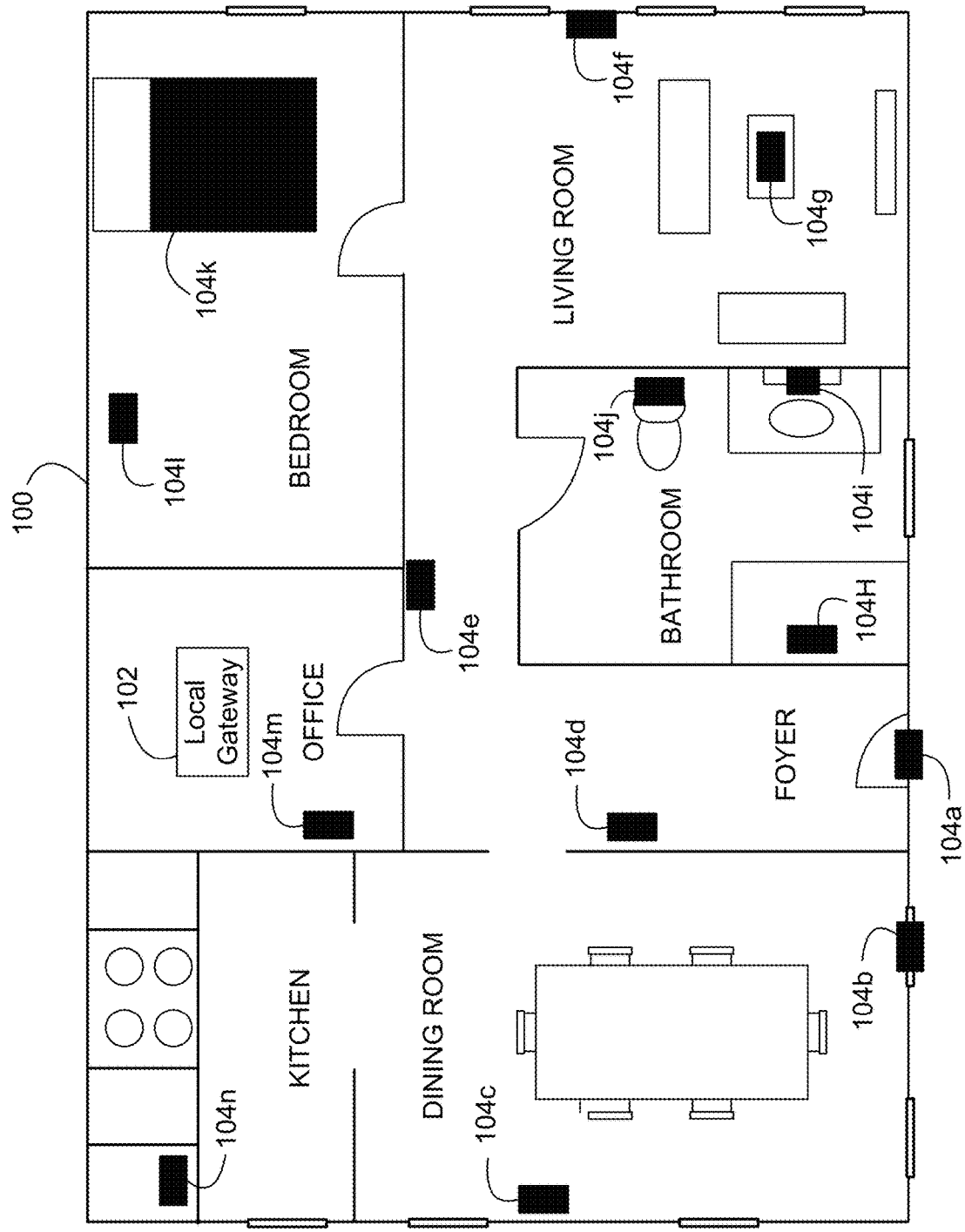
FIG. 1 illustrates a smart monitoring environment according to an embodiment of the present invention.

FIG. 1 illustrates an example of a smart monitoring environment according to an embodiment of the present invention. The depicted smart monitoring environment includes a structure 100, which can include, e.g., a house, office building, assisted living and/or long-term care facility, mobile home, or any other dwelling environment. The smart monitoring environment of FIG. 1 includes a plurality of sensor devices 104a-104n comprised of intelligent-sensing network-connected devices, that can integrate seamlessly with each other and/or with a central server or a cloud-computing system. The depicted structure 100 includes a plurality of rooms where the sensor devices 104a-104n can be mounted on, integrated with and/or supported by a wall, floor, or ceiling.

In some embodiments, sensor devices 104a-104n may comprise room motion sensors, individual safety sensors, individual location sensors, appliance/fixture sensors, and any combination thereof. Room motion sensors may comprise devices that connect a passive infrared sensor (PIR) to a component able to communicate with local gateway 102 via wireless communication technology such as Bluetooth low energy (LE), IEEE 802.11b, or other means of data transmission. In other embodiments, a plurality of local gateways may be deployed to improve coverage and performance in receiving signals from the plurality of sensor devices 104a-104n. For example, a local gateway may be deployed on each floor of a house. A room motion sensor may look for motion in a room and report measurements. For example, sensor devices 104c, 104d, 104f, 104e, 104h, 104l, and 104m, may comprise at least room motion sensors for determining occupancy of given rooms or areas within structure 100. Positioning of room motion sensors can be mapped to a blueprint of the room to increase accuracy of information and help interested parties understand where motion is occurring.

Individual safety sensors may comprise devices that connect a push button to a beacon component able to communicate with local gateway 102 via wireless communication technology. The button of the individual safety sensor may capture and immediately notify interested parties when pushed by the individual, of an emergency or when in need of immediate help. According to one embodiment, during button press of the individual safety sensors, a light-emitting diode (LED) light may illuminate in lock step with button press for comfort feedback. Alternatively, the LED light may blink (as opposed to a steady light) for power conservation and better visual feedback. Blinking of the LED light may further avoid simultaneous LED light and radio power consumption from communication with local gateway 102 by alternating intervals between wireless transmissions and LED light blinking.

Upon button press, a beacon signal may be communicated to local gateway 102. The beacon signal may include button press duration to convey urgency and/or uniquely identify events or devices. Beacon signals may be received by multiple local gateways to improve detection rate. A central server may receive the beacon signals and de-duplicate them from multiple gateways before analysis. An event counter (e.g., number of unique button presses) and button press duration may be used algorithmically by the server to interpret the beacon signals. The central server may include data analytics or artificial intelligence that can be used to interpret button press urgency from the event counter and button press duration. For instance, a brief button press could be interpreted as an accidental button press white repeated rapid or lengthy button presses may indicate urgency and an emergency.

Appliance/fixture sensors may comprise accelerometers connected to a component able to communicate with the local gateway 102 via wireless communication technology. Accelerometer motion detected by the appliance/fixture sensors can indicate certain events. For example, sensor device 104j may be an appliance/fixture sensor mounted on the toilet handle to detect movement, where movement corresponds to an individual flushing the toilet. Other examples of appliance/fixture sensors may include: sensor device 104a adhered to a door can indicate when a door has been opened, closed, or broken; sensor device 104b adhered to a window can indicate when a window has been opened, closed, or broken; sensor device 104n adhered to a kitchen appliance, such as, a refrigerator, can indicate when the refrigerator has been opened and closed; sensor device 104g adhered to an entertainment device, such as, a television remote, can indicate usage/watching of television; and sensor device 104i adhered to a medicine cabinet can indicate an individual taking medicine.

In certain embodiments, the smart monitoring environment may further include near-field sensor devices that may uniquely identify some action with a person (family, caregiver, individual) or object (medication, asset). The near-field sensor devices may detect signals from wireless transmitter devices, such as RFID (radio-frequency identification), worn by or attached to people or objects. For example, a near-field sensor device may notify that a caregiver entered and left the room, or that an individual took medication at a given time. A near-field sensor device may comprise a device that connects a near-field communication (NFC) sensor to a component able to communicate with the local gateway 102 via wireless communication technology.

According to another embodiment, the smart monitoring environment may further include individual motion sensors comprised of a device that connects an accelerometer to a component able to communicate with the local gateway 102 via wireless communication technology. The individual motion sensor may measure the individual's orientation and motion to detect events. For example, the individual motion sensors can detect a possible fall event from values corresponding to measurements of movement matching one or more patterns. Such a sensor can be contained in a waterproof enclosure and, for example, adhered to the back of the individual's collar or similar fixed apparel on the individual whereby there should be little error introduced by motion that is not caused by movement of the body.

Additional types of sensors and actuators can include, but are not limited to: cameras, thermal imaging, bed sensors (e.g., 104k), microphone, speaker, touch screen display, and thermometer/thermostat that may be applied, attached, or integrated with stoves and/or ovens, washers, dryers, indoor or outdoor lighting, stereos, intercom systems, gated entries, garage-door openers, floor fans, ceiling fans, wall air conditioners, pool heaters, irrigation systems, security systems, safes, and so forth. Individual location sensors may comprise devices that identify a current location of an individual and communicates with local gateway 102 via wireless communication technology. For the purpose of improving accuracy, the system can rely on the position of any fixed-location component, such as the local gateway 102 or a room motion sensor. Any of the sensors described herewith may exist independently or be combined in a single enclosure, such as combining an individual location sensor with an individual motion sensor and/or an individual safety sensor.

It should be appreciated that the smart monitoring environment may further include areas outside the home, such as curtilage, the yard, and other nearby land. Further, the smart monitoring environment can control and/or be coupled to devices and sensors outside of the actual structure 100. Several devices in the smart monitoring environment need not physically be within the structure 100. For example, a device controlling an outdoor lighting system or gated entry system can be located outside of the structure 100.

By leveraging multiple sensors, individuals can be monitored within structure 100 for their safety and to improve their quality of life. In addition to containing processing and sensing capabilities, each of the sensor devices are capable of data communications and information sharing with any other of the sensor devices, as well as to any central server or cloud-computing system or any other device. Family and/or caregivers can review information that is collected to determine if the individual is behaving normally or not. As an example, if the individual typically leaves their room three hours per day, but suddenly shows leaving for only one hour per day then those connected to the individual can be notified. Events, such as falls or other potentially life-threatening events, may also be recorded and used to notify families and/or caregivers. Families and/or caregivers can log into a web portal or mobile application to review observed information, trends and notifications generated from the sensor devices. This information may be presented in the form of graphs showing trends, as well as a simple numerical value or score that identifies risk to safety and deviation from normal observations.

Figure 2:
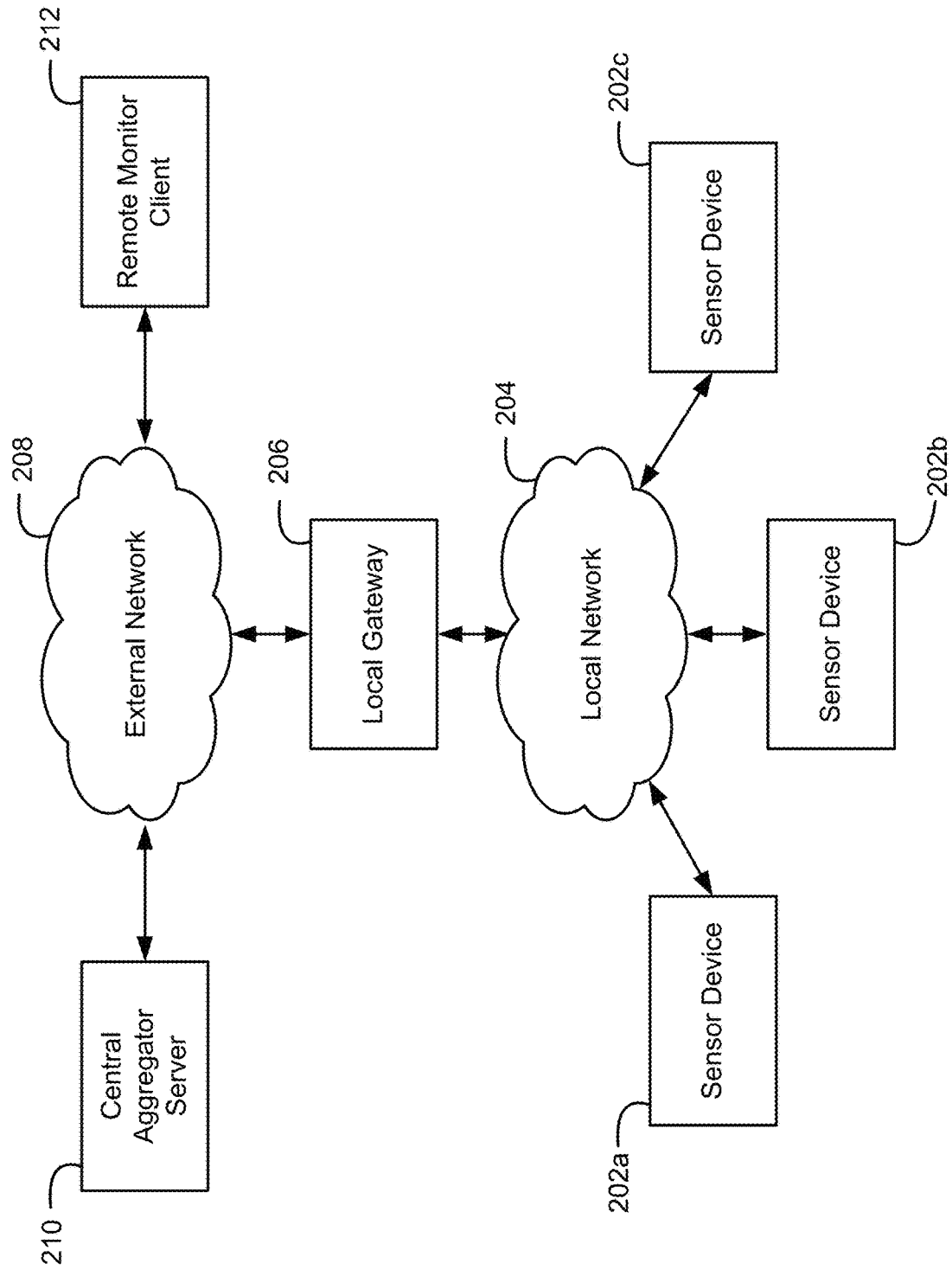
FIG. 2 illustrates a networked system according to an embodiment of the present invention.

FIG. 2 presents a networked system including a plurality of devices from a smart monitoring environment such as the one illustrated in FIG. 1. Sensor devices 202a, 202b, and 202c and local gateway 206 may be installed within a home or facility to monitor elderly or disabled individuals living in the home or facility. Sensor devices 202a, 202b, and 202c can communicate with each other and with local gateway 206 through local network 204 wirelessly via Bluetooth LE, IEEE 802.11b, or other transmission methods. Local gateway 206 may comprise a device at the individual's residence or room that collects information from the sensor devices. The collected information may be communicated through the external network 208 via Ethernet, 802.11 wireless, or other means of transmission, from local gateway 206 to central aggregator server (or cloud-computing system) 210 for storage and processing.

External network 208 may be any suitable type of network allowing transport of data communications across thereof. The external network 208 may couple devices so that communications may be exchanged, such as between servers and client devices or other types of devices, including between wireless devices coupled via a wireless network, for example. A network may also include mass storage, such as network attached storage (NAS), a storage area network (SAN), cloud computing and storage, or other forms of computer or machine readable media, for example. In one embodiment, the network may be the Internet, following known Internet protocols for data communication, or any other communication network, e.g., any local area network (LAN) or wide area network (WAN) connection, cellular network, wire-line type connections, wireless type connections, or any combination thereof. Communications and content stored and/or transmitted to and from client devices may be encrypted using, for example, the Advanced Encryption Standard (AES) with a 256-bit key size, or any other encryption standard known in the art.

The central aggregator server 210 may include data storage and means of data analysis, that collates information gathered by local gateway 206. The central aggregator server 210 can be hosted at the facility or may exist as a cloud-based service. For example, central aggregator server 210 may comprise at least a special-purpose digital computing device including at least one or more central processing units and memory. The special-purpose digital computing device may also include one or more of mass storage devices, power supplies, wired or wireless network interfaces, input/output interfaces, and operating systems, such as Windows Server, Mac OS X, Unix, Linux, FreeBSD, or the like.

Central aggregator server 210 can generate data, statistics, and notifications from the collated information. Data from sensor devices 202a, 202b, and 202c may be analyzed, for example, in combination with rules-based inference engines and/or artificial intelligence and/or any suitable smart environment data. Central aggregator server 210 is operative to receive requests from remote monitor client 212 and process the requests to generate responses to the remote monitor client 212 across the external network 208. Data generated by central aggregator server 210 may be accessed by a remote monitor client 212 using a web portal and/or mobile application. Remote monitor client 212 may be used by families and/or caregivers to review observed information, trends and notifications generated from the sensor devices to monitor an observed individual, such as, a patient or elderly person, to ensure their well-being and safety. For example, family members can check on the individual from their mobile phone, and receive alerts when certain patterns or conditions occur.

The central aggregator server 210 may be associated with a manufacturer, support entity, or service provider associated with the network-connected sensor devices. For one embodiment, a user may be able to contact local law enforcement and other emergency or security personnel as well as contact customer support using one of the network-connected sensor devices itself rather than needing to use other communication means such as a telephone or Internet-connected computer. According to an alternative embodiment, functionality of the central aggregator server 210 may be optionally replaced by the local gateway 206. Such a change effectively decentralizes the data so that local gateway 206 can host the data, present the web portal, and provide a means for a mobile application to communicate with.

Remote monitor client 212 may comprise computing devices (e.g., desktop computers, television set top boxes, terminals, laptops, personal digital assistants (PDA), cell phones, smartphones, tablet computers, e-book readers, smart watches and wearable devices, or any computing device having a central processing unit and memory unit capable of connecting to a network). Client devices may also comprise a graphical user interface (GUI) or a browser application provided on a display (e.g., monitor screen, LCD or LED display, projector, etc.). A client device may also include or execute an application to communicate content, such as, for example, textual content, multimedia content, or the like. A client device may include or execute a variety of operating systems, including a personal computer operating system, such as a Windows, Mac OS or Linux, or a mobile operating system, such as iOS, Android, or Windows Mobile, or the like.

Figure 3:
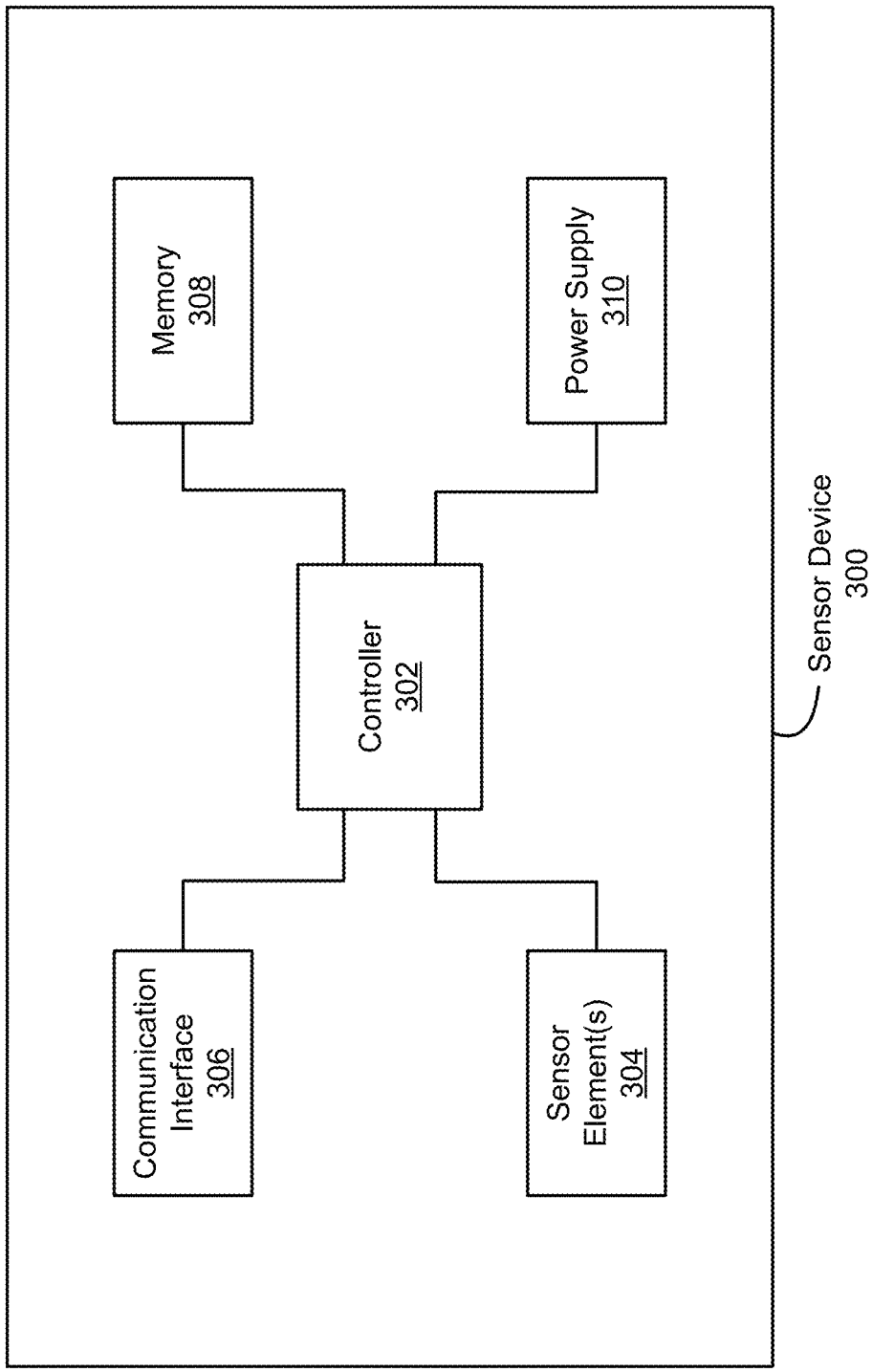
FIG. 3 illustrates a schematic overview of a sensor device according to an embodiment of the present invention.

FIG. 3 presents a schematic overview of a sensor device 300 according to an embodiment of the present invention. Sensor device 300 comprises sensor element(s) 304. According to one embodiment, the sensor device 300 may be an accelerometer-based movement sensor device. For example, sensor 300 may include sensor element(s) 304 comprising a movement sensor element containing an accelerometer and associated movement detection circuiting. As discussed above, the sensor device 300 may contain additional sensors of a different or second type in one or more embodiments. Such second type of sensors may be motion sensors, on-person worn sensors or other sensors known in the art. Such second type sensors may be dedicated sensors used for detecting a specific action that the sensor was designed to detect.

The sensor device 300 further comprises a controller 302, which may be implemented as one or more processors (CPU) or programmable logic circuits (PLC), which is connected to or comprises a memory 308. The memory may be implemented using any commonly known technology for electronic device memories such as read-only memory (ROM), random-access memory (RAM), static RAM (SRAM), dynamic RAM (DRAM), complementary metal-oxide-semiconductor (CMOS), flash memory, synchronous dynamic random-access memory (SDRAM), double data rate (DDR) SDRAM, or some other memory technology. The memory 308 is configured to store a definition of certain patterns to be detected. The sensor device 300 also comprises a communication interface 306. The communication interface may be a wireless radio frequency interface such as a Bluetooth or a IEEE 802.11 standard link. The communication interface 306 may also be a wired interface.

The controller 302 is configured to receive a sensing signal from the sensor element(s) 304 and to compare the signal to the definition of the patterns stored in the memory 308. If the signal matches the pattern, an event is detected. In response to a detected pattern, the controller 302 may be configured to activate the communication interface 306 and transmit a detection signal to one or more local gateways. Wireless communication transmissions from a sensor device 300 may also be increased to improve detection. For example, a sensor device may start at a lower rate for battery conservation and increased gradually or immediately to improve chances of detection and reduce time of detection.

The sensor device 300 may be powered by a power supply 310, such as a battery, a solar cell or other power supply. In certain embodiments, a sensor device may increase transmission power to improve detection during button presses (e.g., individual safety sensors). For example, the sensor device may start at a lower transmission power for battery conservation and gradually or immediately increase transmission power to improve a chance to detect transmissions from the sensor device. For example, a gradual increase may include a transmission at −20 dBm to −4 dBm and then to +4 dBm; and an immediate increase may include a transmission at −20 dBm to +4 dBm. Increases in transmission power during button presses may also be used to improve triangulation. For example, sensor devices may transmit a few signals at a variety of increasing power levels over time. Transmission power levels of sensor devices may be collected and used in analytics. Signals transmitted from sensor devices may also include event counters, tokens or identifiers to unique identify events from each sensor device at local gateways. The event counters, tokens or identifier may also help distinguish separate button presses (e.g., short press vs. long press, single-press vs. double-press, etc.).

Figure 4:
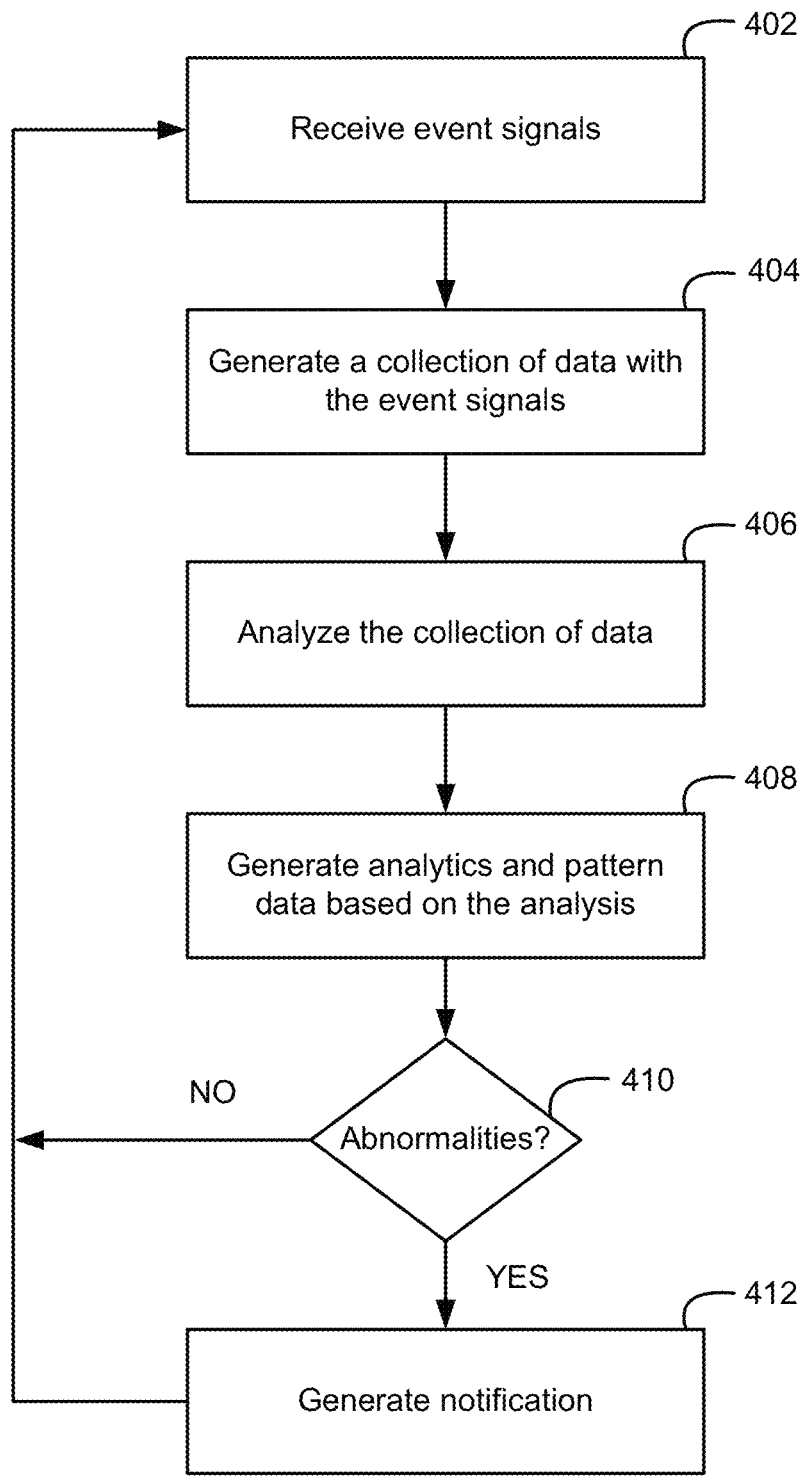
FIG. 4 illustrates a flowchart of a method for analyzing data received from devices of a smart monitoring environment according to an embodiment of the present invention.

FIG. 4 presents a flowchart of a method for analyzing data received from devices of a smart monitoring environment according to an embodiment of the present invention. One or more event signals are received by a computing device such as a central aggregator server (or a local gateway in certain embodiments), step 402. The signals may be an aggregation of signals from sensor devices of a smart monitoring environment. A given signal received by the computing device may include data or indications of events associated with a specific function of a sensor device (e.g., motion, presence, location, usage, an alert, etc.).

A collection of data is generated with the event signals, step 404. The collection of data may be stored in a database. The collection of data including the event signals is analyzed by the computing device, step 406. The analysis may include determining trends associated with health and safety conditions from the event signals such as behaviors in eating, sleeping, mobility, hygiene, to name a few. Data from the event signals may be correlated with the trends based on rules and/or artificial intelligence.

Analytics and pattern data are generated based on the analysis of the collection of data, step 408. The analytics and pattern data may include logs, charts, graphs, and warnings based on the results of the analysis. The presence of abnormalities in the analytics and pattern data are determined by the computing device, step 410. The computing device generates a notification if there is a presence of abnormalities, such as warnings, in the analytics and pattern data, step 412.

Figure 5:
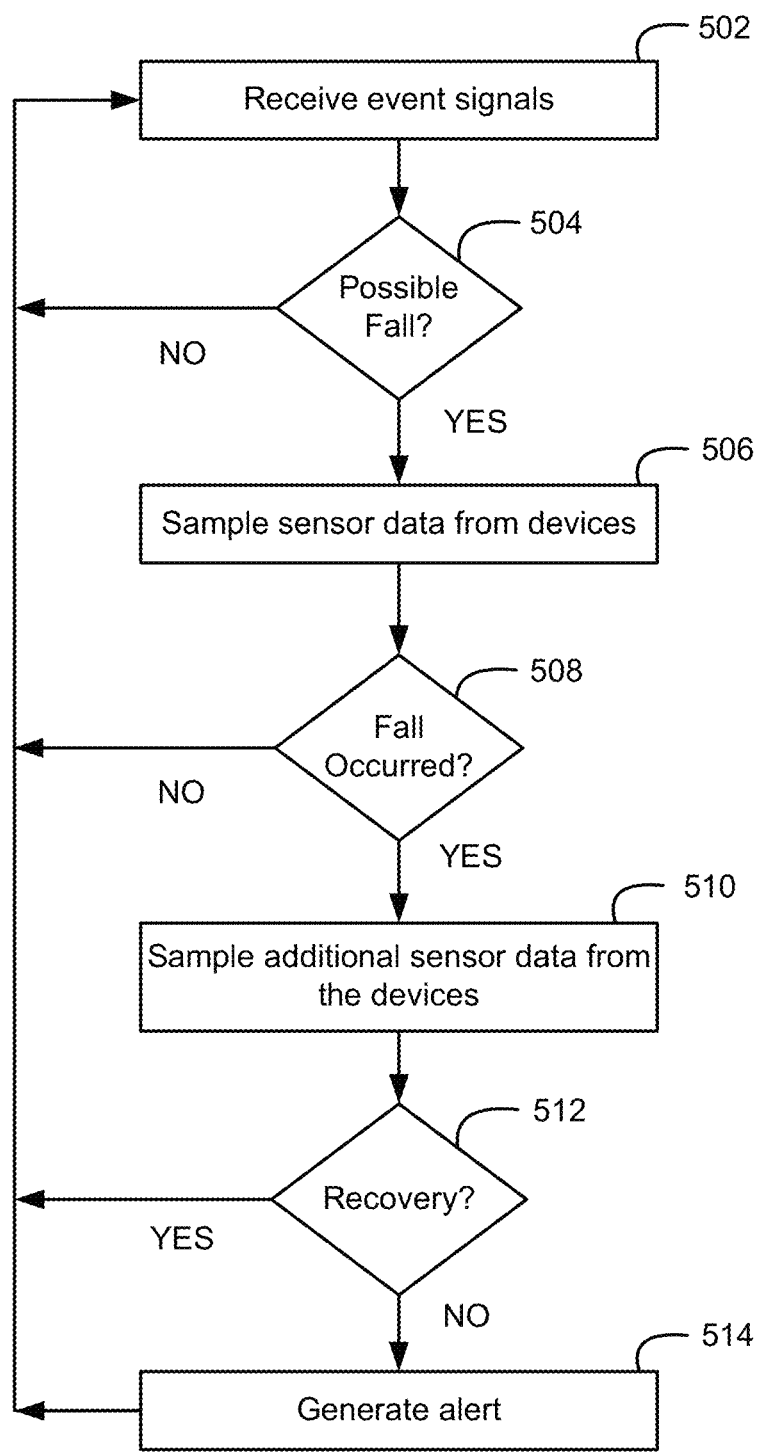
FIG. 5 illustrates a flowchart of a method for detecting falls from devices of a smart monitoring environment according to an embodiment of the present invention.

FIG. 5 presents a flowchart of a method for detecting falls from sensor devices of a smart monitoring environment according to an embodiment of the present invention. The sensor devices in the smart monitoring environment may include accelerometer or movement detection circuits/sensors operable to measure the magnitude of movements. A computing device may be connected to the sensor devices via a wireless network connection. The computing device may be any device including at least one processor and memory capable of connecting to a network, such as a server, or a cloud computing host. The computing device receives one or more event signals from sensor devices, step 502.

The computing device may listen for and identify a possible fall event from one or more of the sensor devices based on the one or more event signals, step 504. A possible fall event may comprise sensor data including values that exceed a threshold, e.g., activity values that are greater than a predetermined amount or for more than a given duration of time. Upon receiving and identifying a possible fall event, sensor data from the one or more of the sensor devices are sampled by the computing device, step 506. For example, if sensors in a room detect a possible fall event, the computing device may poll or listen for sensor data from the sensors in the room, near the region, or within a zone of the possible fall event (e.g., near a toilet) and for a period of time. The sensor data may comprise values corresponding to measurements of movement detected by the sensor devices. The measurements may be in real-time or at the moment the possible fall event had occurred. According to one embodiment, the measurements may comprise a delta sum of the absolute displacement values of movement along a plurality of coordinate axis (e.g., x, y, z). The devices may transmit a stream of sensor data to the computing device at a predetermined frequency. Sampling the sensor data may include selecting a portion of the stream of sensor data from the sensor devices, the portion being for a given time window (e.g., a few hundred milliseconds or seconds).

The computing device determines whether a fall has occurred based on the sampled sensor data, step 508. The computing device may evaluate the sensor data to determine whether it falls in a range that confirms that the person has indeed fallen. The sampled sensor data may include a plurality of movement measurements within a given time window that can be compared with patterns. Alternatively, machine learning classifiers may be used to identify fall events from the sampled sensor data. The machine learning classifiers may be trained by labeling a training set of sensor data using the patterns.

The patterns may be stored in a database or memory accessible or connected to the computing device and include characteristics for interpreting magnitudes of movement within the given time window in the sampled sensor data. For example, the patterns may correspond to movements corresponding to a fall with recovery (e.g., where a sufferer is able to get back up), a fall without recovery (e.g., where the sufferer becomes unconscious), or non-fall events. According to another embodiment, the patterns may correspond to other events, such as seizures, heart attacks, panic attacks, choking, or other life-threatening events. The sampled sensor data may be correlated with the patterns based on rules and/or machine learning and artificial intelligence.

If it is determined that a fall has not occurred, the computing device returns to receiving event signals to listen for a possible fall event, step 502. Otherwise, if a fall has occurred, additional sensor data is sampled from the one or more of the sensor devices, step 510. The computing device may sample real-time sensor data from the sensor devices, e.g., for a few more seconds to determine if there is any more motion. Additional motion may indicate that the person has gotten up or recovered from the fall. Conversely, the absence of motion may indicate that the person is unconscious or unable to get up.

A determination is made whether the person has recovered from the fall, step 512. If additional motion is detected in a sufficient amount to indicate that the person has gotten up or recovered from the fall, the computing device returns to receiving event signals to listen for a possible fall event, step 502. However, if the person has not recovered from the fall (e.g., lack of additional motion), an alert is generated, step 514. The alert may be transmitted to a central monitoring location, an emergency contact, medical staff, care provider, or a call operator. According to an alternative embodiment, either outcome in step 512 may cause an alert to be generated to notify that a fall has occurred and may trigger assistance services.

Figure 6:
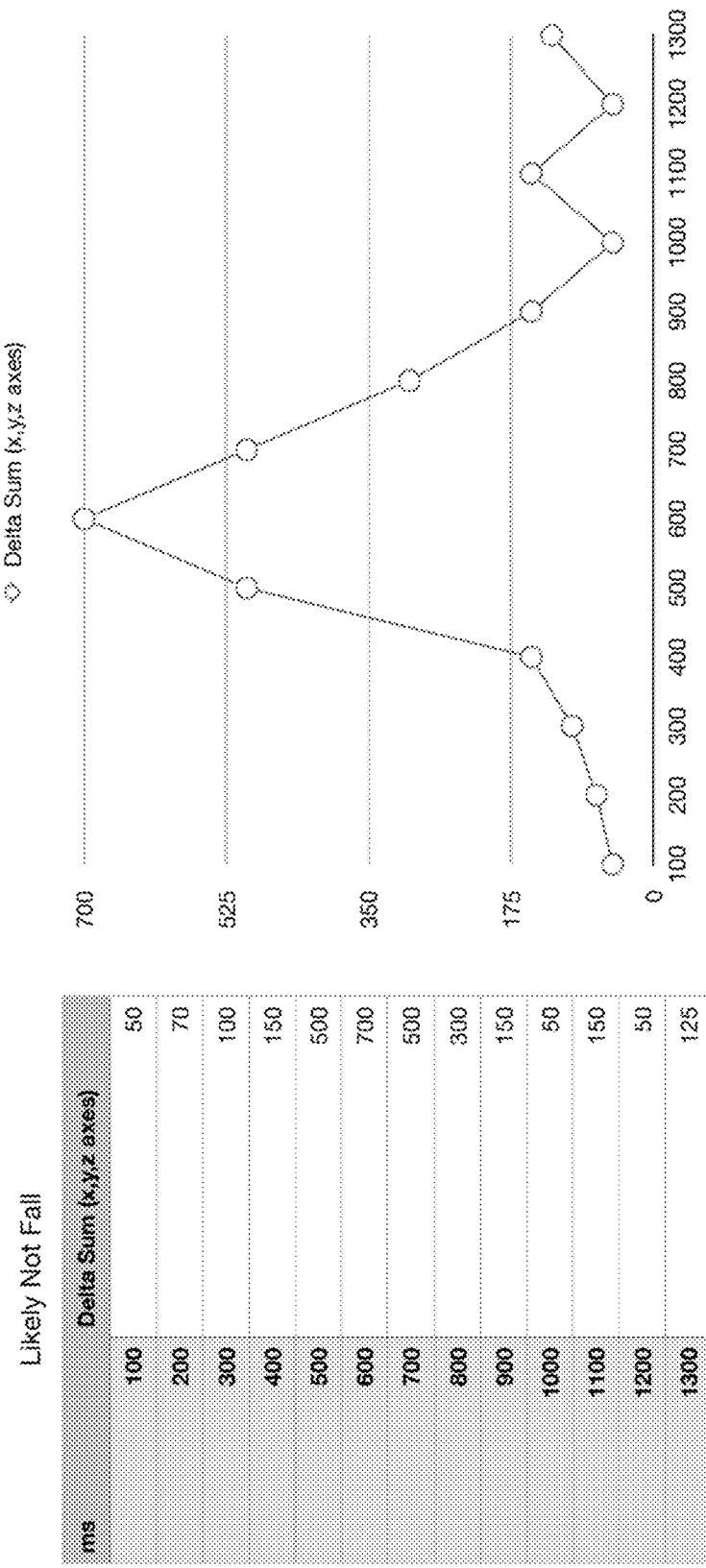
FIG. 6 illustrates exemplary sensor data for an event not likely to be a fall according to an embodiment of the present invention.

FIG. 6 presents exemplary sensor data for an event not likely to be a fall according to an embodiment of the present invention. Sensor data may be received from a device that records a delta sum of movements over time. A duration of an event in milliseconds (ms) and amplitude of movement (e.g., Delta Sum along x, y, or z axis) may be recorded. The illustrated sensor data includes a rapid, transient change in the amplitude of movement from a baseline value from 500 ms to 800 ms. Such a change in the delta sum of movements may be within normal operating conditions or attributed to noise based on the short duration.

Figure 7:
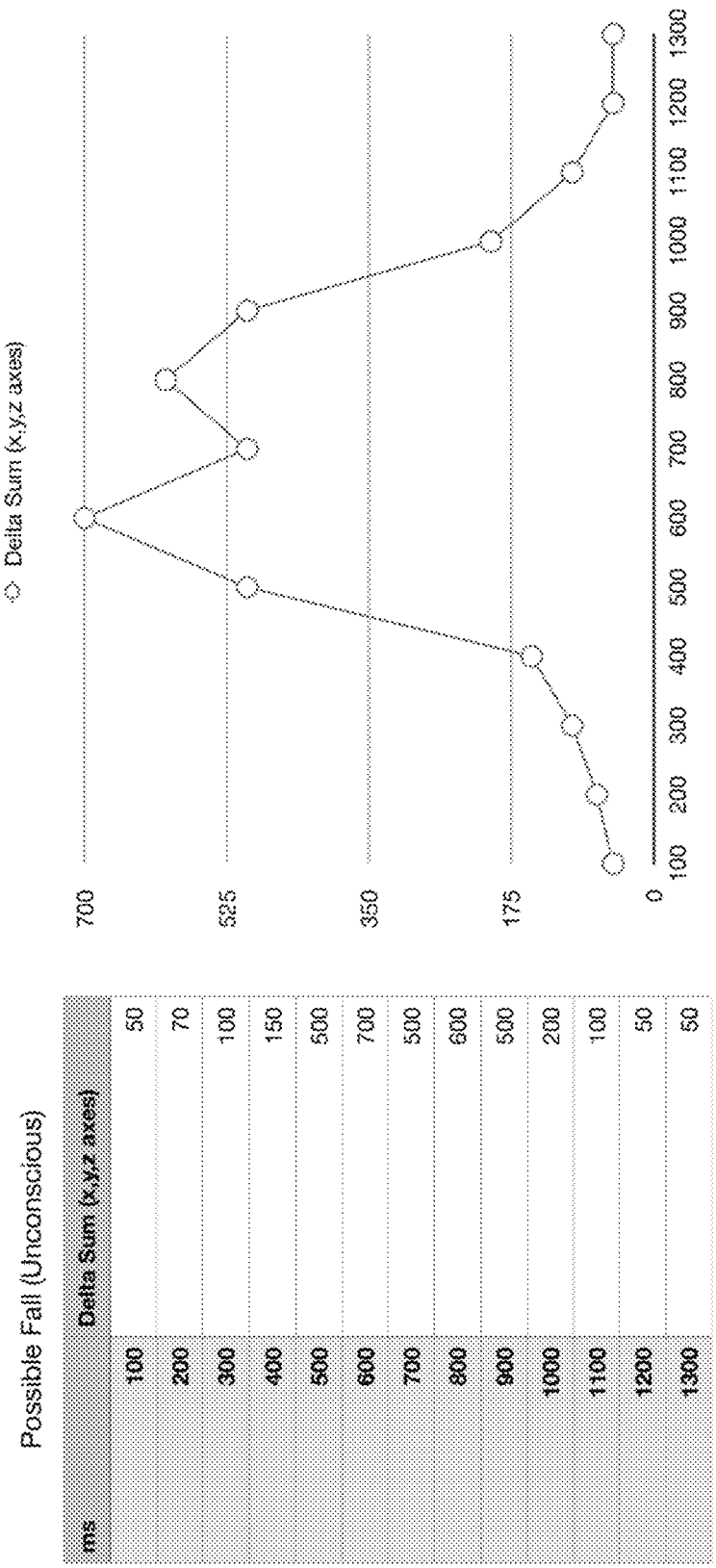
FIG. 7 illustrates exemplary sensor data for a possible fall according to an embodiment of the present invention.

FIG. 7 presents exemplary sensor data for a possible fall according to an embodiment of the present invention. The illustrated sensor data includes a pronounced change in the amplitude of movement from a baseline value from 500 ms to 900 ms. This data signature may indicate that a person has fallen and has not moved after the initial fall. Such an event may require special attention and cause an alert or notification to be generated.

Figure 8:
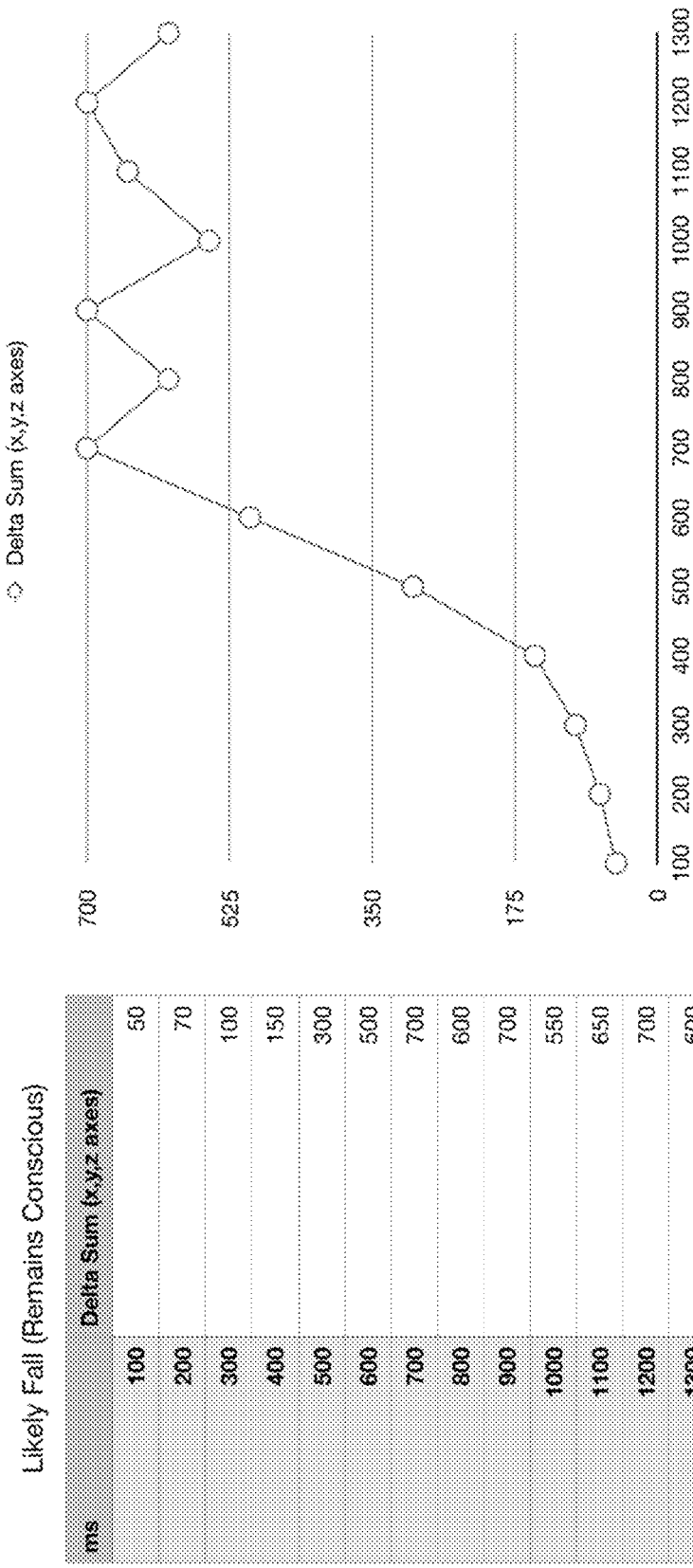
FIG. 8 illustrates exemplary sensor data for a likely fall according to an embodiment of the present invention.

FIG. 8 presents exemplary sensor data for a likely fall according to an embodiment of the present invention. Another type of fall may be depicted by the illustrated sensor data. As illustrated, a sustained increase in the amplitude of movement occurs from 500 ms to 1300 ms. Such activity may indicate a fall with recovery (e.g., getting up from the fall). In certain embodiments, sensor data indicating a likely fall may be used to trigger an alarm or assistance from, for example, a monitoring center.

FIGS. 1 through 8 are conceptual illustrations allowing for an explanation of the present invention. Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

It should be understood that various aspects of the embodiments of the present invention could be implemented in hardware, firmware, software, or combinations thereof. In such embodiments, the various components and/or steps would be implemented in hardware, firmware, and/or software to perform the functions of the present invention. That is, the same piece of hardware, firmware, or module of software could perform one or more of the illustrated blocks (e.g., components or steps). In software implementations, computer software (e.g., programs or other instructions) and/or data is stored on a machine readable medium as part of a computer program product, and is loaded into a computer system or other device or machine via a removable storage drive, hard drive, or communications interface. Computer programs (also called computer control logic or computer readable program code) are stored in a main and/or secondary memory, and executed by one or more processors (controllers, or the like) to cause the one or more processors to perform the functions of the invention as described herein. In this document, the terms "machine readable medium," "computer readable medium," "computer program medium," and "computer usable medium" are used to generally refer to media such as a RAM; a ROM; a removable storage unit (e.g., a magnetic or optical disc, flash memory device, or the like); a hard disk; or the like.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

What is claimed is:

1. A smart monitoring system, the system comprising:
   a processor; and
   a memory having executable instructions stored thereon that when executed by the processor cause the processor to:
   receive event signals from a first accelerometer that is configured to measure activity values corresponding to movements of a person;
   receive a location signal from an individual location sensor that is configured to measure a location of the person;
   identify a possible fall event based on activity values included in the event signals received from the first accelerometer exceeding a threshold;
   identify a current location of the person based on the location signal received from the individual location sensor;
   sample first sensor data from the first accelerometer based on the activity values exceeding the threshold, the first sensor data including values representative of measurements of movement associated with the possible fall event;
   determine that a fall has occurred to the person based on the sampled first sensor data;
   sample second sensor data from a second accelerometer for additional motion at a period of time subsequent to the fall based on the determination that a fall has occurred, the second accelerometer being selected based on the identified current location of the person, the additional motion comprising a sustained increase in an amplitude of movement;
   determine a presence of recovery from the fall based on the second sensor data including the additional motion; and
   generate trends associated with health and safety conditions including behaviors in mobility based on the determination of the fall, the presence of recovery, and the event signals.

2. The system of claim 1 wherein the processor is further configured to:
   determine an absence of the recovery from the fall based on the second sensor data; and
   generate an alert based on the absence of the recovery.

3. The system of claim 2 wherein the processor is further configured to transmit the alert to at least one of a central monitoring location, emergency contact, medical staff, care provider, and a call operator.

4. The system of claim 1 wherein the first sensor data includes real-time measurements of movement of the person.

5. The system of claim 1 wherein the first sensor data includes measurements of movement of the person at a time of occurrence of the fall.

6. The system of claim 1 wherein the measurements of movement of the person comprise a delta sum of absolute displacement values of movement along a plurality of coordinate axis.

7. The system of claim 1 wherein the processor is further configured to compare the measurements of movement of the person within a given time window with one or more patterns.

8. The system of claim 7 wherein the one or more patterns correspond to movements associated with events selected from the group consisting of: a fall with recovery, a fall without recovery, or non-fall events.

9. The system of claim 1 wherein the second sensor data is received from a plurality of sensor devices, and at least one of the plurality of sensor devices are attached to appliances and fixtures that are selected from the group consisting of a toilet, a door, a window, a refrigerator, a television remote, and a medicine cabinet.

10. The system of claim 9 wherein the processor is further configured to:
receive the second sensor data from a sensor device coupled to a handle of the toilet; and
determine a flushing of the toilet based on the second sensor data received from the sensor device coupled to the handle of the toilet.

11. The system of claim 9 wherein the processor is further configured to:
receive the second sensor data from a sensor device coupled to the door; and
determine an opening or closing of the door based on the second sensor data received from the sensor device coupled to the door.

12. The system of claim 9 wherein the processor is further configured to:
receive the second sensor data from a sensor device coupled to the window; and
determine an opening or closing of the window based on the second sensor data received from the sensor device coupled to the window.

13. The system of claim 9 wherein the processor is further configured to:
receive the second sensor data from a sensor device coupled to the refrigerator; and
determine an opening or closing of the refrigerator based on the second sensor data received from the sensor device coupled to the refrigerator.

14. The system of claim 9 wherein the processor is further configured to:
receive the second sensor data from a sensor device coupled to the television remote; and
determine watching of a television based on the second sensor data received from the sensor device coupled to the television remote.

15. The system of claim 9 wherein the processor is further configured to:
receive the second sensor data from a sensor device coupled to the medicine cabinet; and
determine an individual taking medicine based on the second sensor data received from the sensor device coupled to the medicine cabinet.

16. A method, in a data processing system comprising a processor and a memory, the method comprising:
receiving, by a computing device, event signals from a first accelerometer that is configured to measure activity values corresponding to movements of a person;
receiving, by the computing device, a location signal from an individual location sensor that is configured to measure a location of the person;
identifying, by the computing device, a possible fall event based on activity values included in the event signals received from the first accelerometer exceeding a threshold;
identifying, by the computing device, a current location of the person based on the location signal received from the individual location sensor;
sampling, by the computing device, first sensor data from the first accelerometer based on the activity values exceeding the threshold the first sensor data including values representative of measurements of movement associated with the possible fall event;
determining, by the computing device, that a fall has occurred to the person based on the sampled first sensor data;
sampling, by the computing device, second sensor data from a second accelerometer for additional motion at a period of time subsequent to the fall based on the determination that a fall has occurred, the second accelerometer being selected based on the identified current location of the person, the additional motion comprising a sustained increase in an amplitude of movement;
determining, by the computing device, a presence of recovery based on the second sensor data including the additional motion; and
generating trends associated with health and safety conditions including behaviors in mobility based on the determination of the fall, the presence of recovery, and the event signals.

17. The method of claim 16 further comprising:
determining an absence of the recovery from the fall based the second sensor data; and
generating an alert based on the absence of the recovery.

18. The method of claim 17 further comprising transmitting the alert to at least one of a central monitoring location, emergency contact, medical staff, care provider, and a call operator.

19. The method of claim 16 wherein the measurements of movement of the person comprise a delta sum of absolute displacement values of movement along a plurality of coordinate axis.

20. A non-transitory computer readable medium storing instructions that, when executed by a hardware processor, cause the hardware processor to:
receive event signals from a first accelerometer that is configured to measure activity values corresponding to movements of a person;
receive a location signal from an individual location sensor that is configured to measure a location of the person;
identify a possible fall event based on activity values included in the event signals received from the first accelerometer exceeding a threshold;
identify a current location of the person based on the location signal received from the individual location sensor;
sample first sensor data from the first accelerometer based on the activity values exceeding the threshold, the first sensor data including values representative of measurements of movement associated with the possible fall event;
determine that a fall has occurred to the person based on the sampled first sensor data;
sample second sensor data from a second accelerometer for additional motion at a period of time subsequent to the fall based on the determination that a fall has occurred, the second accelerometer being selected based on the identified current location of the person, the additional motion comprising a sustained increase in an amplitude of movement;
determine a presence of recovery from the fall based on the second sensor data including the additional motion; and
generate trends associated with health and safety conditions including behaviors in mobility based on the determination of the fall, the presence of recovery, and the event signals.

* * * * *